United States Patent [19]

Miwa et al.

[11] 4,401,967
[45] Aug. 30, 1983

[54] GAS SENSOR

[75] Inventors: Naoto Miwa, Tsushima; Yoshihiro Segawa, Okazaki, both of Japan

[73] Assignee: Nippondenso Co., Ltd., Kariya, Japan

[21] Appl. No.: 286,345

[22] Filed: Jul. 23, 1981

[30] Foreign Application Priority Data

Jul. 30, 1980 [JP] Japan .......................... 55-108262[U]
Jul. 31, 1980 [JP] Japan .......................... 55-108729[U]

[51] Int. Cl.³ ............................................. H01L 7/00
[52] U.S. Cl. .................................... 338/34; 73/27 R; 422/98
[58] Field of Search ......................... 338/34; 73/27 R; 324/65 R; 422/83, 88, 98; 23/232 E

[56] References Cited

U.S. PATENT DOCUMENTS 3,959,765  5/1976  Stewart ................................. 338/34
4,147,513  4/1979  Bienkowski et al. ............. 23/232 E
4,320,378  3/1982  Tamiguchi et al. ................... 338/34
4,322,968  4/1982  Takami et al. ..................... 338/34 X Primary Examiner—B. A. Reynolds
Attorney, Agent, or Firm—Cushman, Darby & Cushman

[57] ABSTRACT

A gas sensor is disclosed which comprises a sintered metal oxide the resistance value of which changes with the ambient temperature, a gas sensor element having at least one electrode connected to the sintered metal oxide, a ceramic insulator for insulatively holding the gas sensor, a lead connection and a lead wire connected between the electrodes. The diameter of the ceramic insulator for passing the lead wire is reduced and the length of the electrode is shortened, thus realizing a compact gas sensor.

17 Claims, 12 Drawing Figures

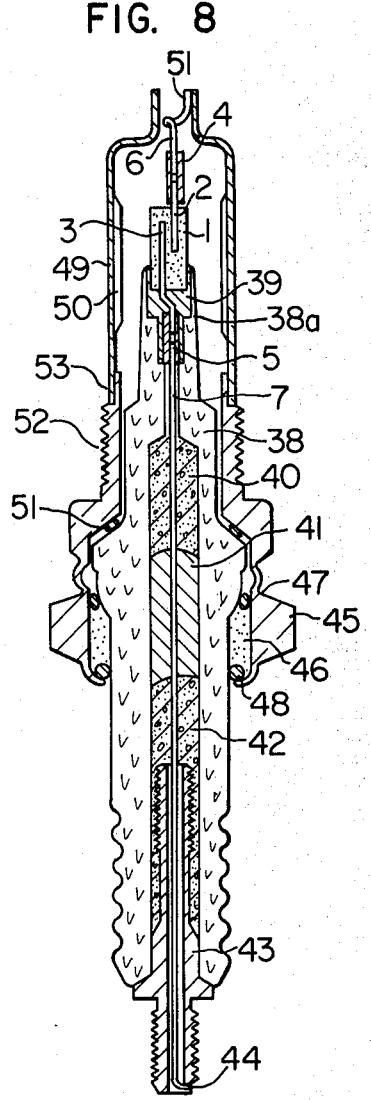
FIG. 8
FIG. 9
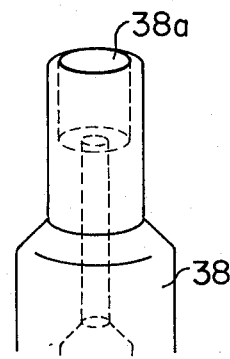
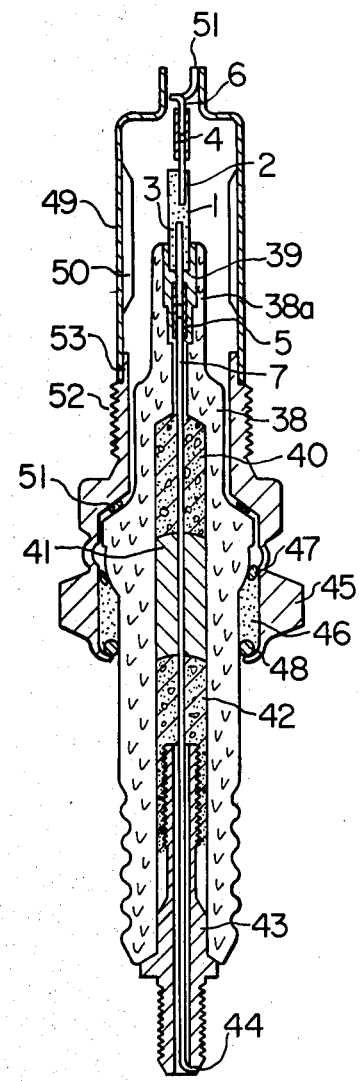
FIG. 10

GAS SENSOR

BACKGROUND OF THE INVENTION

1. Field of the Invention

This invention relates to a gas sensor adapted for use with an exhaust gas purification system of an automobile or the like using a three-way catalyst.

2. Description of the Prior Art

A well-known gas sensor is disclosed in U.S. Pat. No. 3,959,765 Specification. This device comprises a sensor element of a transition metal oxide in sintered form, a pair of electrodes embedded in the sensor element, a ceramic member including a pair of small holes for accommodating the pair of electrodes and a pair of large through holes for accommodating a pair of lead pins for taking out the change of the resistance value of the sensor element, and means of electrical conduction made of a conductive glass interposed between the electrodes and the lead pins.

A further study of the gas sensor of the conventional construction shows that it has the problems described below.

(1) In order to uniformly fill the conductive glass in the electrical connection between the lead pins and the electrodes, the lead pins are required to be driven into the conductive glass to press the conductive glass when being melted. This in turn requires a lead pin of large diameter for increasing the pressing area thereof, with the result that the ceramic member large in diameter is required, thus leading to a bulky sensor.

(2) A precious metal such as platinum high in heat resistance and anticorrosiveness is used for the electrode pair. This conventional electrode pair is unnecessarily long and high in cost.

SUMMARY OF THE INVENTION

Accordingly, it is an object of the present invention to provide a compact gas sensor in which the electrodes of the gas sensor are connected to lead wires by lead connection so that the diameter of the lead wire is greatly reduced thereby to reduce the diameter of a ceramic insulator into which the lead wires are inserted, without using conductive glass.

Another object is to shorten the length of the electrodes by using a lead connection, thus greatly reducing the cost of the gas sensor.

A further object is to provide a compact and light-in-weight gas component detector by using a single lead wire secured within the ceramic insulator.

A still further object of the invention is to provide a gas sensor in which one each of the electrodes of the gas sensor element is connected with each end of a sintered metal oxide thereby to avoid the reduction in the insulating resistance between the electrodes which otherwise might occur due to the residual materials in the object gas.

BRIEF DESCRIPTION OF THE DRAWINGS

FIG. 8 is a sectional view showing a sixth embodiment of the present invention.

FIG. 9 is a perspective view of the leg portion of the ceramic insulator shown in FIG. 8.

FIG. 10 is a sectional view showing a seventh embodiment of the present invention.

DESCRIPTION OF THE PREFERRED EMBODIMENTS

The present invention will now be explained with reference to the preferred embodiments in conjunction with the accompanying drawings.

Figure 1:
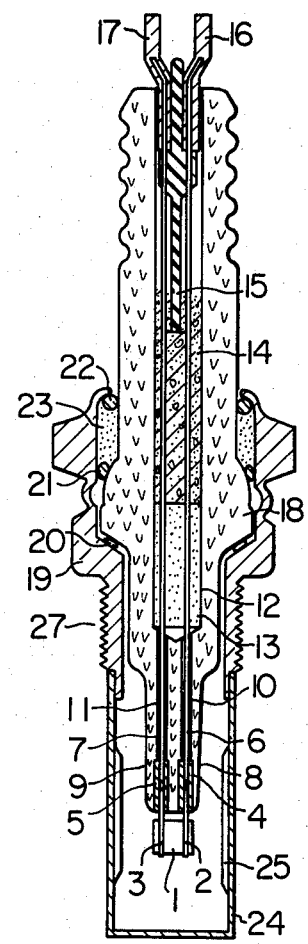
FIG. 1 is a sectional view showing a first embodiment of the gas sensor according to the present invention.

A sectional view of the first embodiment of a gas sensor according to the present invention is shown in FIG. 1.

In FIG. 1, the gas sensor comprises a pair of electrodes 2 and 3 embedded in spaced relation with each other in a transition metal oxide in sintered form designated by reference numeral 1. The sintered transition metal oxide 1 is made of titanium oxide, cobalt oxide, tin oxide, zirconium oxide, zinc oxide or the like the resistance value of which changes according to the gas composition, for example, oxygen composition. The electrodes 2 and 3 of the gas sensor element are electrically connected through lead wires 6 and 7 of stainless steel and tubular lead connections 4 and 5 of stainless steel respectively. The other end each of the lead wires 6 and 7 is connected to the terminals 16 and 17 outside of a ceramic insulator 18. The lead connections 4 and 5 are accommodated and positioned respectively in holes 8 and 9 formed in the leg portion of the ceramic insulator 18. The lead wires 6 and 7 are passed through a pair of holes 10 and 11 formed in the ceramic insulator 18 in electrically insulated relation with each other on the one hand and are secured with borosilicate, non-alkali lead glass 13 and cement 14 on the other hand. The cement 14 which is made of Sumiceram, Aronceramic (trade names) or the like secures a spacer 15 of an electrically insulating material (alumina) together with the lead wires 6 and 7.

A metal housing 19 for holding the ceramic insulator 18 is fixedly caulked by use of a metal packing 20, metal rings 21, 22 and ceramic powder 23 by a well-known method used for spark plugs. Numeral 27 designates a screw thread to be secured to the wall of the object gas passage (such as an exhaust gas tube), which screw thread is provided on the housing 19. This screw thread 27 may be replaced by a flange with equal effect. A cover 24 for protecting the gas sensor element is electrically and mechanically secured to the forward end of the housing 19. An object gas flow path 25 in louver form (or circular form) is provided in the side of the cover 24 for controlling the flow of the object gas.(The opening of this louver is invisible as the sectional view thereof is limited). The lead wires 6, 7, the connections 4, 5 and the electrodes 2, 3 are integrally coupled with each other in advance followed by the insertion of the lead wires 6 and 7 through the holes 10 and 11.

The operation of the gas sensor according to the present invention will be described below.

Figure 2:
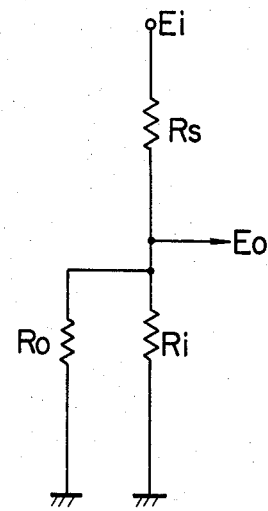
FIG. 2 is a diagram showing an equivalent electric circuit for explaining the operation of a gas sensor according to the present invention.

In FIG. 2, a constant voltage Ei is applied in series to a reference resistor Rs and a sensor resistor Ri thereby to produce an output voltage Eo at a point intermediate between the reference resistor Rs and the sensor resistor Ri. Depending on the operating conditions, a resistor Ro of about 1 to 10 MΩ may be connected in parallel to the resistor Ri when the resistor Ri is large in value.

Figure 3:
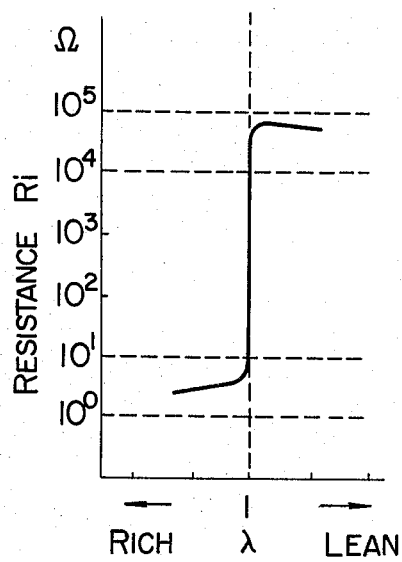
FIG. 3 shows a change in resistance value of a sensor element used with the gas sensor according to the present invention.

In FIG. 3, when the sensor element is exposed to an object gas, the resistance value thereof changes according to the normalized air-fuel ratio (λ) of the air-fuel mixture supplied to an engine. This resistance value is detected by the pair of electrodes 2 and 3.

In FIG. 1, the current flows through the terminal 16, the lead wire 6, the lead connection 4, the electrode 2, the sintered metal oxide 1, the electrode 3, the lead connection 5, the lead wire 7 and the terminal 17 in that order. When Ei is 8 V, for instance, the output Eo of 0.1 V is detected when the normalized air-fuel ratio (λ) is smaller than 1, and the output Eo of 7.8 V is detected when the normalized air-fuel ratio (λ) is larger than 1.

Figure 4A:
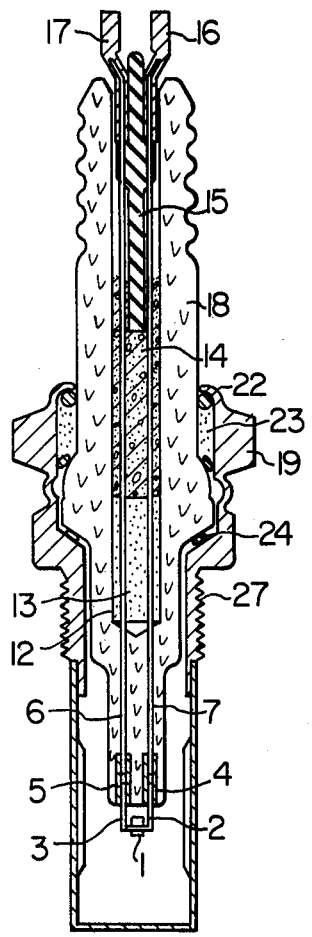
FIG. 4A is a sectional view of a second embodiment of the gas sensor according to the present invention.
Figure 4B:
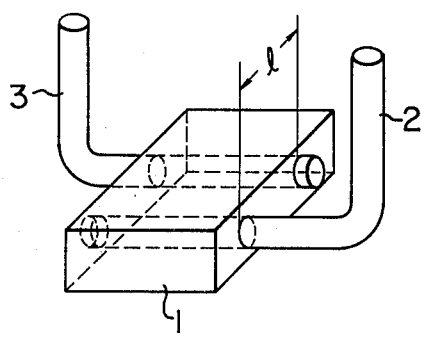
FIG. 4B is a perspective view of a gas sensor used in the embodiment of FIG. 4A.

FIG. 4A shows a second embodiment of the present invention in which the sintered metal oxide in FIG. 1 is reduced in size and the sides of the electrodes 2 and 3 which are connected to the sintered metal oxide 1 are bent as shown in FIG. 4B. The electrodes 2 and 3 are fixed at an interval l in the sintered metal oxide 1.

Figure 5:
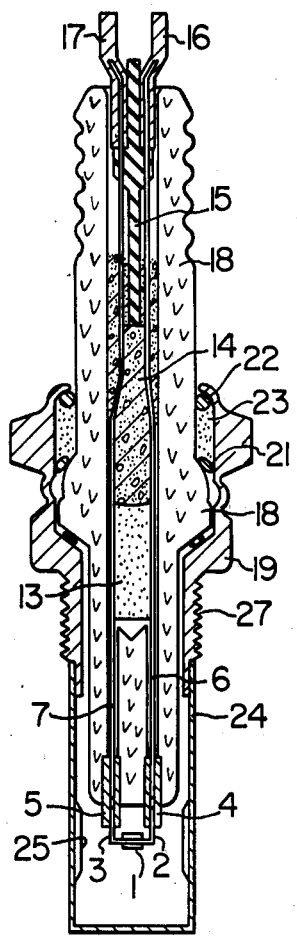
FIG. 5 is a sectional view of a third embodiment of the present invention.

A sectional view of a third embodiment of the present invention is shown in FIG. 5. In FIG. 5, the lead connections 4 and 5 are projected from the leg portion of the ceramic insulator 18 by a weldable length of 2 to 3 mm for laser welding, and the projected sides thereof are connected to the electrodes 2 and 3. The electrodes 2 and 3 are bent in a manner similar to FIG. 4B, and fixed at an interval of l to each other in the sintered metal oxide 1.

Figure 6A:
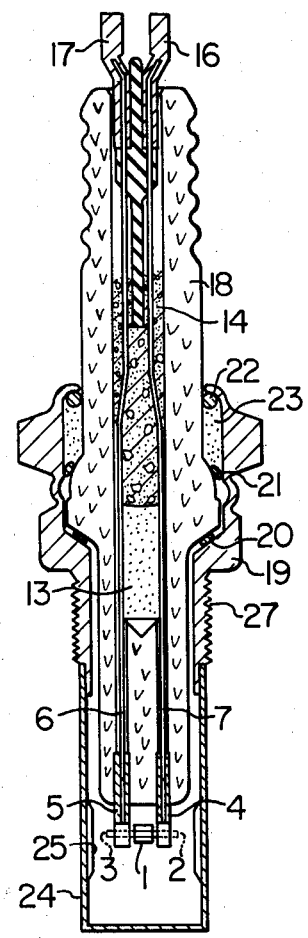
FIG. 6A is a sectional view of a fourth embodiment of the present invention.
Figure 6B:
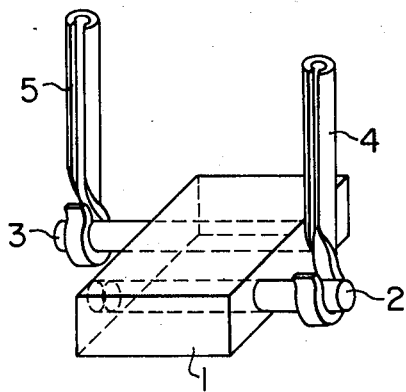
FIG. 6B is a perspective view of a gas sensor element used in the embodiment of FIG. 6A.

A sectional view of a fourth embodiment of the present invention is shown in FIG. 6A. In FIG. 6A, the lead connections 4 and 5 are projected from the leg portion of the ceramic insulator 18 by a weldable length such as 2 to 3 mm for the laser welding, and the electrodes 2 and 3 are welded by being held by the bent portions of the lead connections 4 and 5 as shown in FIG. 6B.

Figure 7:
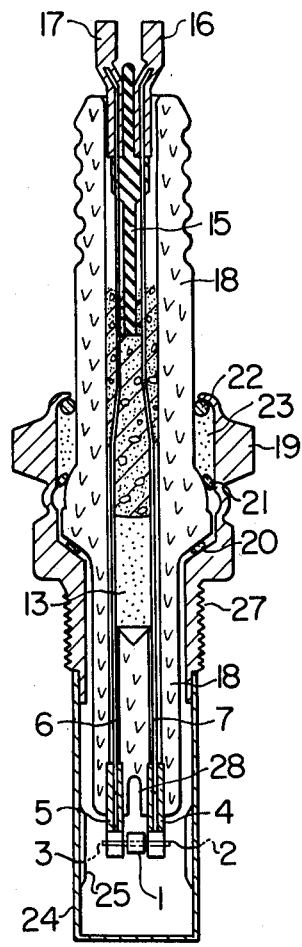
FIG. 7 is a sectional view of a fifth embodiment of the present invention.

FIG. 7 shows a fifth embodiment of the present invention which includes a partial improvement of the embodiment of FIG. 6A. In this improvement, the leg portion of the ceramic insulator 18 is provided with a slot 28 for lengthening the gap between the lead connections 4 and 5. According to this embodiment, the creeping distance between the connections 4 and 5 is lengthened by the slot 28, thus preventing the reduction in resistance which otherwise might occur due to foreign matters attached to the particular portion. In conventional constructions, the insulation is reduced to 1 MΩ at the rate of 10% during the period of 200 hours, when the normalized air-fuel ratio (λ) is 0.8 and the surrounding temperature is 800° C. The construction according to the present invention, by contrast, maintains more than 20 MΩ without any reduction in insulation ability. In the embodiment under consideration, the electrodes 2 and 3 are connected with the connections 4 and 5 in the same manner as in FIG. 6B.

A sixth embodiment of the present invention is shown in FIG. 8. In FIG. 8, the gas sensor element comprises a pair of electrodes 2 and 3 embedded in spaced relation to each other in the transition metal oxide in sintered form. The embedded portions of the electrodes 2 and 3 are opposed parallelly in spaced relation to each other. The sintered transition metal oxide 1 is made of such a material as titanium oxide, cobalt oxide, tin oxide, zirconium oxide or zinc oxide which changes in resistance value according to the gas composition. The electrodes 2 and 3 on the other hand are made of Pt-Rh and Pt respectively. The positive electrode 3 of the gas sensor element is electrically connected by the stainless lead wire 7 and the stainless tubular lead connection 5, and the end of the lead wire 7 is connected securely electrically and mechanically at the forward end 44 of the metal stem 43 making up a positive terminal.

A perspective view of the leg portion of the ceramic insulator of FIG. 8 is shown in FIG. 9.

As shown in FIG. 9, the gas sensor element is such that the positive electrode 3 is hermetically secured by means of an electrically insulating bonding material such as cement or glass 39 in the hole 38a (having a larger diameter than the sintered metal oxide 1) of the leg portion of the ceramic insulator 38 not to be exposed to the gas to be detected. The lead wire 7 is mechanically bonded with the cement 40 and the glass 41 in the ceramic insulator 38. The stem 43 which has a central hole for passing the lead wire 7 is fixedly held on the ceramic insulator 38 by cement 42. The glass 41 is made of borosilicate, non-alkali, lead glass or the like, while the cement 42 comprises Sumiceram or Aronceramic (trade names). The metal housing 45 for holding the ceramic insulator 38 is secured to the outer periphery of the ceramic insulator 18 by means of a packing 51, and rings 47 and 48 by a well-known method used for spark plugs. Numeral 52 shows a screw thread provided on the housing 45 for fixing to the wall of the passage of the object gas such as on an exhaust gas tube. This screw thread 52 may be replaced by a flange with equal effect. The metal cover 49 for protecting the detector element is electrically and mechanically secured to the forward end 53 of the housing 45. An object gas flow path 50 in louver form (or in circular form) for controlling the flow of the object gas is formed in the side of the cover 49. The earth or ground electrode 2 of the sensor element is fixed electrically and mechanically to the forward end 51 of the cover by means of the lead connection 4 and the coil lead wire 6. The opening of the flow path 50 is not visible as the sectional view thereof is limited.

The operation of the gas sensor according to the sixth embodiment of the present invention will be described. Upon insertion of the sensor element into an object gas, the resistance value changes by the normalized air-fuel ratio λ as shown in FIG. 3. This resistance value is detected by the pair of electrodes 2 and 3. Basically, the circuit operates in such a manner that as shown in FIG. 2, the constant voltage Ei is applied in series to the reference resistor Rs and the sensor resistor Ri thereby to produce an output voltage Eo at an intermediate point of the reference resistor Rs and the sensor resistor Ri. Depending on the operating conditions involved, a resistor Ro of about 1 to 10 MΩ may be added in parallel to the resistor Ri in case of the resistor Ri being increased. The current flows through the stem 43, the lead wire 7, the lead connection 5, the positive electrode 3, the sintered transition metal oxide 1, the earth electrode 2, the lead connection 4, the coil lead 6, the cover 49 and the housing 45 in that order, and is grounded through the screw thread 52 of the housing 45. When the voltage Ei is 8 V, for instance, the voltage Eo is given as 0.2 V for a rich air-fuel mixture, and 7.5 V for a lean air-fuel mixture.

In the embodiment under consideration, one electrode each is connected to each of the ends of the sintered metal oxide with the electrodes having a considerable spatial interval therebetween, and therefore the insulating resistance between the electrodes is not reduced even when a compound of carbon, iron or lead is deposited on the electrodes.

Further, in view of the fact that the positive electrode 3 of the gas sensor element is hermetically sealed within the recess 38a of the ceramic insulator 38 by means of the electrically insulating bonding agent 39 not to be exposed to the object gas, the insulation resistance between the positive electrode 3 and the housing 45 is not reduced even if a considerable amount of carbon or the like is deposited on the leg portion of the ceramic insulator 38.

A sectional view of a seventh embodiment of the present invention is shown in FIG. 10. In FIG. 10, the construction of the sensor element is different from that of the sixth embodiment shown in FIG. 8. Specifically, the pair of electrodes 2 and 3 are provided in opposed relation to each other within the transition metal oxide. The operation of this embodiment is the same as that of the embodiment shown in FIG. 8.

As explained in detail above, the present invention has the great advantages as follows:

(1) The electrodes of the gas sensor element are connected to the lead wires by a lead connection and thus the use of conductive glass is eliminated unlike the prior art, so that the diameter of the lead wires is remarkably reduced as compared with the conventional devices and therefore the diameter of the ceramic insulator for passing the lead wire is reduced, thus reducing the size of the sensor;

(2) The use of the lead connection shortens the length of the electrodes, thereby extremely decreasing the cost of the sensor;

(3) In view of the construction of the gas sensor element in which one each of the electrodes is connected to each of the ends of the sintered metal oxide, the spatial interval between the electrodes is lengthened, thus minimizing the decreases in the insulation resistance between the electrodes caused by the residual materials in the object gas.

We claim:

1. A gas sensor comprising a sintered metal oxide with the resistance value thereof changing according to the gas component, a gas sensor element including at least one electrode embedded in said sintered metal oxide, a ceramic insulator for insulatively holding said gas sensor element, means for securing at least one lead wire within said ceramic insulator, and a lead connection connected to the electrode of said gas sensor element and having a tubular portion supported in said insulator and connected to the lead wire.

2. A gas sensor according to claim 1, further comprising at least a hole in said insulator for accommodating said lead connection, and at least second hole formed in said ceramic insulator and communicating with said accommodating hole, said lead wire being inserted in said second hole on the one hand and connected to the lead connection accommodated in said accommodating hole on the other hand.

3. A gas sensor according to claim 2, wherein the connected end of said electrode and said lead wire are coaxial.

4. A gas sensor according to claim 2, wherein that portion of said electrode which is outside said oxide is bent.

5. A gas sensor according to claim 2 or 3, wherein said lead connection is projected from said ceramic insulator, and said electrode is connected to the end of said projection.

6. A gas sensor according to claim 5, wherein there are two electrodes and two connections and a slot is formed between the lead connections in the end of the leg portion of said ceramic insulator.

7. A gas sensor according to claim 1, further comprising a metal housing secured to the outer periphery of said ceramic insulator and a metal cover secured to said metal housing, enclosing said element and having an object gas flow path and including two electrodes embedded in each of the ends of said sintered metal oxide, one of said electrodes being connected electrically to said lead wire, the other of said electrodes being electrically connected to said metal housing through said metal cover.

8. A gas sensor according to claim 7, wherein that portion of said one of the electrodes exterior of the oxide is prevented from being exposed to the object gas by being positioned in a recess in said ceramic insulator and being covered by an electrically insulating bonding material.

9. A gas sensor according to claim 7 or 8, wherein said electrodes are embedded in parallel within said sintered metal oxide.

10. A gas sensor according to claim 8, wherein said at least one of the electrodes is embedded in parallel within said sintered metal oxide, and said parallel portion is not included in said electrically insulating bonding material.

11. A gas sensor according to claim 7 or 8, wherein the electrodes are in spaced generally coaxial relation to each other within said sintered metal oxide.

12. A gas sensor according to claim 8, wherein at least one of the electrodes is embedded in opposed relation within the sintered metal oxide, and the opposed portion is not included in said electrically insulating material.

13. A gas sensor according to claim 1, wherein said lead connection is made of stainless steel.

14. A gas sensor according to claim 7, wherein said lead wire is twisted.

15. A gas sensor according to claim 7, wherein said sintered metal oxide is cylindrical.

16. A gas sensor according to claim 8, wherein said sintered metal oxide is cylindrical and held by said electrically insulating material in the recess of said ceramic insulator.

17. A gas sensor according to claim 7 wherein there is a hole in the end part of the metal cover and one of the lead wires is connected to the cover in said hole.

* * * * *